US008834407B2

(12) United States Patent
Greeson, Jr. et al.

(10) Patent No.: US 8,834,407 B2
(45) Date of Patent: Sep. 16, 2014

(54) COVERED YANKAUER SUCTION DEVICE AND METHODS OF USING SAME

(75) Inventors: Dale F. Greeson, Jr., Palatine, IL (US); Marc A. Lessem, Highland Park, IL (US); Patricia M. Risty, Arlington Heights, IL (US); Alberto C. Savage, Buffalo Grove, IL (US); Earl D. Wilson, Ingleside, IL (US)

(73) Assignee: Medline Industries, Inc., Mundelein, IL (US)

( * ) Notice: Subject to any disclaimer, the term of this patent is extended or adjusted under 35 U.S.C. 154(b) by 1406 days.

(21) Appl. No.: 11/509,917

(22) Filed: Aug. 24, 2006

(65) Prior Publication Data

US 2007/0173764 A1    Jul. 26, 2007

Related U.S. Application Data

(60) Provisional application No. 60/760,476, filed on Jan. 20, 2006.

(51) Int. Cl.
*A61N 1/30* (2006.01)
*A61M 1/00* (2006.01)

(52) U.S. Cl.
CPC .................................. *A61M 1/008* (2013.01)
USPC .............................................. 604/19; 604/35

(58) Field of Classification Search
USPC ........................... 604/19, 35, 171; 433/91, 95
See application file for complete search history.

(56) References Cited

U.S. PATENT DOCUMENTS

| 1,120,549 | A |   | 12/1914 | Schellberg |
|---|---|---|---|---|
| 1,581,508 | A |   | 4/1926 | Bomhard |
| 3,894,540 | A |   | 7/1975 | Bonner, Jr. |
| 3,902,500 | A |   | 9/1975 | Dryden |
| 3,924,608 | A |   | 12/1975 | Mitsui |
| 4,058,896 | A |   | 11/1977 | Moore |
| D264,246 | S |   | 5/1982 | Ekbladh et al. |
| 4,397,640 | A |   | 8/1983 | Haug et al. |
| 4,468,217 | A |   | 8/1984 | Kuzmick et al. |
| 4,573,979 | A |   | 3/1986 | Blake |
| 4,652,259 | A | * | 3/1987 | O'Neil .................. 604/544 |
| 4,691,702 | A |   | 9/1987 | Chantzis |
| 4,741,326 | A |   | 5/1988 | Sidall et al. |
| 4,960,412 | A |   | 10/1990 | Fink |
| 5,073,164 | A |   | 12/1991 | Hollister et al. |
| 5,083,561 | A |   | 1/1992 | Russo |
| 5,125,893 | A |   | 6/1992 | Dryden |
| 5,134,996 | A |   | 8/1992 | Bell |
| 5,140,983 | A |   | 8/1992 | Jinotti |

(Continued)

FOREIGN PATENT DOCUMENTS

| JP | 4054960 | 2/1992 |
|---|---|---|
| WO | WO93/21984 | 11/1993 |
| WO | WO96/30069 | 10/1996 |

*Primary Examiner* — Kevin C. Sirmons
*Assistant Examiner* — Deanna K Hall
(74) *Attorney, Agent, or Firm* — Nixon Peabody LLP

(57) ABSTRACT

A covered yankauer suction device is protectable from contamination after use. The covered yankauer suction device includes a yankauer having a suction tip at a first end and a connector at a second end. A retractable sleeve partially encloses the yankauer. One end of the retractable sleeve is secured to the yankauer while the opposite end of the retractable sleeve is secured to a valve. The valve includes a cross-cut that enables the valve to open when the suction tip of the yankauer pushes against the underside of the cross-cut.

13 Claims, 2 Drawing Sheets

(56) References Cited

U.S. PATENT DOCUMENTS

| | | |
|---|---|---|
| 5,149,326 A | 9/1992 | Woodgrift et al. |
| 5,220,916 A | 6/1993 | Russo |
| 5,254,098 A | 10/1993 | Ulrich et al. |
| 5,325,850 A | 7/1994 | Ulrich et al. |
| 5,333,606 A | 8/1994 | Schneider et al. |
| 5,334,149 A | 8/1994 | Nortman et al. |
| 5,343,857 A | 9/1994 | Schneider et al. |
| 5,349,950 A | 9/1994 | Ulrich et al. |
| 5,370,610 A | 12/1994 | Reynolds |
| 5,406,939 A | 4/1995 | Bala |
| 5,460,613 A | 10/1995 | Ulrich et al. |
| 5,464,397 A | 11/1995 | Powers, Jr. |
| 5,490,503 A | 2/1996 | Hollister |
| 5,513,628 A | 5/1996 | Coles et al. |
| 5,527,297 A | 6/1996 | Paul |
| 5,569,202 A | 10/1996 | Kovalic et al. |
| 5,582,161 A | 12/1996 | Kee |
| 5,582,165 A | 12/1996 | Bryan et al. |
| 5,598,840 A | 2/1997 | Iund et al. |
| 5,613,954 A | 3/1997 | Nelson et al. |
| 5,685,836 A | 11/1997 | DiPerna et al. |
| 5,695,474 A | 12/1997 | Daugherty |
| 5,715,815 A | 2/1998 | Lorenzen et al. |
| 5,725,501 A | 3/1998 | Lichtenberg |
| 5,775,325 A | 7/1998 | Russo |
| 5,779,687 A | 7/1998 | Bell et al. |
| 5,791,337 A | 8/1998 | Coles et al. |
| 5,836,918 A | 11/1998 | Dondlinger |
| 5,868,701 A | 2/1999 | Powers, Jr. |
| 5,904,699 A | 5/1999 | Schwemberger et al. |
| 6,068,476 A | 5/2000 | Point |
| 6,129,547 A | 10/2000 | Cise et al. |
| 6,258,065 B1 | 7/2001 | Dennis et al. |
| 6,471,667 B1 | 10/2002 | Epstein |
| 6,500,142 B1 * | 12/2002 | Harreld et al. ............ 604/35 |
| 6,543,451 B1 | 4/2003 | Crump et al. |
| 6,547,724 B1 | 4/2003 | Soble et al. |
| 6,588,427 B1 | 7/2003 | Carlsen et al. |
| 6,632,091 B1 | 10/2003 | Cise et al. |
| 6,702,789 B1 | 3/2004 | Owens et al. |
| 6,712,789 B1 | 3/2004 | Lange et al. |
| 6,860,869 B2 | 3/2005 | Dennis |
| 6,908,428 B2 | 6/2005 | Aizenfeld et al. |
| 6,908,429 B2 | 6/2005 | Heimberger |
| 6,923,184 B1 | 8/2005 | Russo et al. |
| 6,986,773 B1 | 1/2006 | Manougian |
| 6,997,867 B2 | 2/2006 | Soble et al. |
| 7,056,303 B2 | 6/2006 | Dennis et al. |
| 7,625,207 B2 | 12/2009 | Hershey et al. |
| 2001/0044600 A1 | 11/2001 | Elkins |
| 2002/0107484 A1 | 8/2002 | Dennis et al. |
| 2004/0067169 A1 | 4/2004 | Krause |
| 2004/0082923 A1 | 4/2004 | Field |
| 2004/0164043 A1 | 8/2004 | Hakim |
| 2004/0171990 A1 | 9/2004 | Dennis et al. |
| 2004/0182390 A1 | 9/2004 | Owens et al. |
| 2004/0182393 A1 | 9/2004 | MacMillan et al. |
| 2004/0186429 A1 | 9/2004 | Owens et al. |
| 2005/0273063 A1 | 12/2005 | Hoell et al. |
| 2005/0279359 A1 | 12/2005 | LeBlanc et al. |
| 2006/0088800 A1 | 4/2006 | Neff et al. |
| 2006/0100481 A1 | 5/2006 | Soble et al. |
| 2007/0173764 A1 | 7/2007 | Greeson et al. |

* cited by examiner

COVERED YANKAUER SUCTION DEVICE AND METHODS OF USING SAME

CROSS-REFERENCE TO RELATED APPLICATION

This application claims the benefit of U.S. Provisional Application No. 60/760,476, filed Jan. 20, 2006, which is hereby incorporated by reference in its entirety.

FIELD OF THE INVENTION

This invention relates to suction devices for medical purposes, and more specifically to covered yankauer suction devices.

BACKGROUND OF THE INVENTION

Suction devices, such as covered yankauer suction devices, for aspirating fluids from the body are well known. Such suction devices typically include an elongated suction tube, which is connectable at one end to a source of suction. The other end typically includes a tip having one or more holes leading to the suction tube to aid in aspiration as the suction device is being used.

One problem associated with prior suction devices is contamination. Suction devices are typically used over a period of time, and once initially used, the device is contaminated. Without protecting the suction device, it can become contaminated by ambient contaminants and transfer those contaminants to the patient during subsequent use of the device. Conversely, whatever microorganisms or viruses the patient hosts can be passed from the suction device to whatever surface the device is laid upon between uses. Accordingly, once the suction device has been used on a sick patient, the suction device has historically been disposed of because contamination can be transferred from the patient to others. Therefore, if the suction device will be used repeatedly on the same patient, it is important that the suction device be protected in some manner, both to protect the patient as well as others.

In the past, suction devices used in surgical settings have been protected from contamination by providing a clean or sterile surface, such as an instrument tray, upon which the suction device can be placed between uses. This method generally eliminates passage of contaminants from the patient. However, as the suction device is open to the ambient surroundings between uses, it is still subject to contamination by the ambient conditions. Additionally, in non-surgical settings, the suction device is frequently placed in an unclean and non-sterile environment between uses, such as a patient's bed, nightstand or a specially designed holder. Accordingly, contamination can be passed back to the patient the next time that the suction device is used.

Some prior art devices combat the above-identified issues by providing a suction device which can be protected from contamination after use. For example, one known device includes an elongated suction tube having a suction tip at one end. A retractable, protective sheath is connected to the tube and extendable over the exposed length of the tube. A closure is secured to one end of the sheath. The closure includes a cap which can be pivoted to a closed position. To avoid contamination, this device provides an automatic closure to pivot the cap to a closed position. However, the closure on this device rarely, if ever, truly closes. Furthermore, the closure includes far too many components and is unnecessarily complex to address the previously-identified contamination issues.

It would, thus, be desirable to have a protected suction device that addresses the above-identified issues.

SUMMARY OF THE INVENTION

A covered yankauer suction device that is protectable from contamination after use is disclosed. The covered yankauer suction device includes a yankauer having a suction tip at a first end and a connector at a second end. A retractable sleeve partially encloses the yankauer. One end of the retractable sleeve is secured to the yankauer while the opposite end of the retractable sleeve is secured to a valve. The valve includes a cross-cut that enables the valve to open when the suction tip of the yankauer pushes against an underside of the cross-cut.

A covered yankauer suction device that is protectable from contamination after use is disclosed according to an alternative embodiment. The covered yankauer suction device includes a yankauer having a suction tip at a first end and a connector at a second end. A retractable sleeve at least partially encloses the yankauer. One end of the retractable sleeve is secured to the yankauer while the opposite end of the retractable sleeve is secured to a valve. The valve is adapted to slidably and frictionally engage the yankauer.

Additionally, a method for using a covered yankauer suction device is disclosed. The method includes gripping the yankauer near the connector and sliding the valve along the yankauer towards the connector. The valve is adapted to passively lock to the yankauer after the sliding of the valve.

The above summary of the present invention is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

Figure 1:
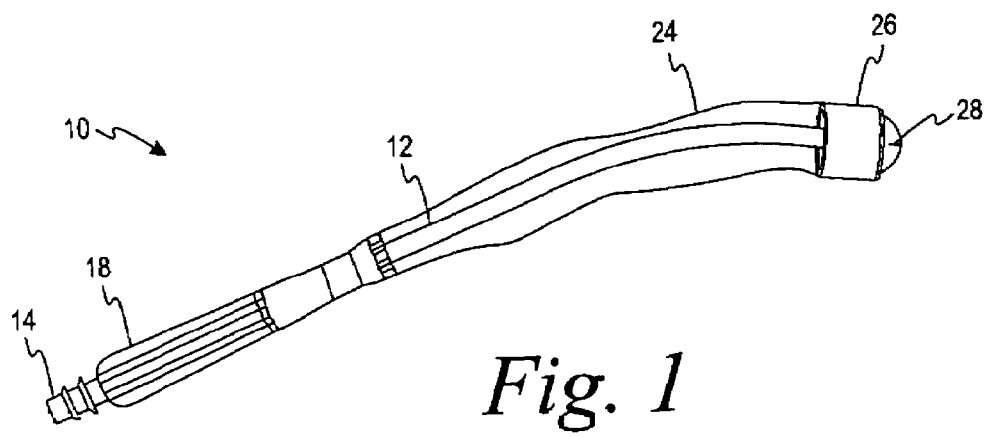
FIG. 1 is a side view of the covered yankauer suction device when not in use.

While this invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

The term "yankauer," as used herein, is a medical term used to refer to any number of tubes that used to suction fluids during a medical procedure. Referring initially to FIG. 1, a covered yankauer suction device 10, according to one embodiment, is illustrated. The covered yankauer suction device 10 includes a yankauer 12. The yankauer 12 is terminated at one end by a connector 14 and by a suction tip 16 (FIG. 2) at the other end. The connector 14 is adapted to associate with a vacuum source (not illustrated) to provide a suction force through the yankauer 12 and the suction tip 16. The connector 14 can be connected directly to the yankauer 12, or, as illustrated, the connector 14 can form part of a handle 18 which is connected to the yankauer 12. The yankauer 12 may or may not include a vent at or near the handle 18. In some embodiments, the connection(s) between the connector 14, the handle 18, and the yankauer 12 can be permanent connection(s). In other embodiments, the connection(s) can be a mechanical connection such as a force fit, a snap fit, a screw fit, a twist lock, adhesive, cohesive, combinations thereof, and/or other connections.

Figure 2:
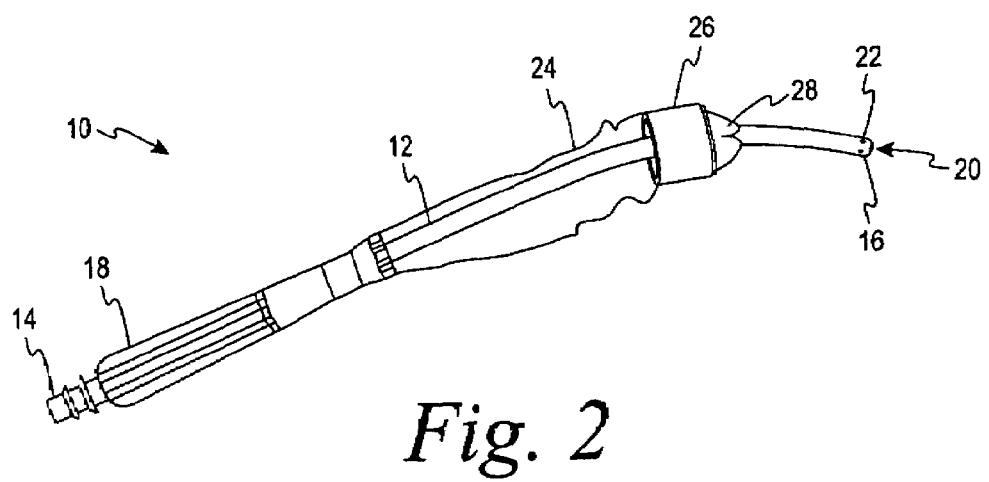
FIG. 2 is a side view of the covered yankauer suction device when in use.

The suction tip 16 of the yankauer 12 includes an end aperture 20 and one or more radial apertures 22, as best seen in FIG. 2. Primary suction is through the end aperture 20, but if that aperture becomes clogged, suction can be through the radial aperture(s) 22. Also, the radial aperture(s) 22 relieve suction if the end aperture 20 is inadvertently pushed against something that effectively seals the end aperture 20.

Returning now to FIG. 1, the covered yankauer suction device 10 also includes a retractable perforated or non-perforated sleeve 24 that surrounds and encloses at least a portion of the yankauer 12. The sleeve 24 is affixed to the handle 18 at one end and to a valve 26 at the other end. The sleeve 24 should be affixed to the handle 18 and the valve 26 to prevent inadvertent separation and to keep the portion of the yankauer 12 within the sleeve 24 enclosed from the atmosphere. However, the sleeve 24 can also be affixed above (i.e., to the yankauer 12 itself) or below the handle 18 and the valve 26 so long as at least a portion of the yankauer 12 is enclosed from the atmosphere. Methods to affix the sleeve 24 to the handle 18 and/or the yankauer 12 and the valve 26 include using an adhesive(s), sonic welding, heat shrinking, a shrink band(s), cohesive, an elastic band(s), ultra-sonic welding, radio frequency (RF) welding, hot melt, and/or heat seal. The sleeve 24 protects the yankauer 12 from contamination when the covered yankauer suction device 10 is not in use. In some embodiments, the sleeve 24 is formed of a pliable plastic material. Alternatively, other materials adapted to protect the yankauer 12 from contamination, such as polyethylene, polyvinyl chloride (PVC), and/or knit, woven and/or non-woven fabric(s) may be used. The material chosen for the sleeve 24 may depend on the level of manipulation required by clinicians, the cost of materials, the ability of the materials to withstand sterilization (if needed), the method of packaging, the weight of the material, the barrier properties, resilience to damage, bonding characteristics, flexibility, other physical properties, etc.

Figure 3:
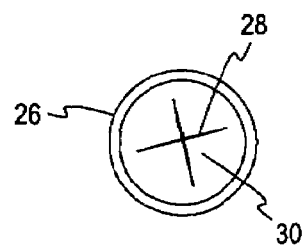
FIG. 3 is a front view of one embodiment of the valve.

The valve 26, to which one end of the sleeve 24 may be connected, initially encloses the yankauer 12 when not in use as illustrated in FIG. 1. The valve 26 can be a single component or include multiple components. Additionally, the valve 26 can be a flexible or rigid body that connects to one end of the sleeve 24 either internally or externally. As shown, the valve 26 includes a cross-cut 28 and corresponding flaps 30, as can be seen in FIG. 3. The flaps 30 open when the suction tip 16 is pushed against the underside of the flaps 30 or the cross-cut 28. Furthermore, the flaps 30 slidably and frictionally engage the yankauer 12 when in use, as illustrated in FIG. 2 and which will be discussed below in more detail. The flaps 30 enable the valve 26 to slidably and frictionally engage the yankauer 12 when in use and enclose the yankauer 12 when not in use. In some embodiments, the valve 26 is comprised of a flexible material such as silicone. Other materials that may be used for the valve 26 include, but are not limited to, thermoplastic elastomer(s), natural rubber (latex), polyester, nylon, polyisoprene, nitrile, urethane, combinations thereof, and/or other suitable materials. The material chosen for the valve 26 may depend on the ease with which the valve 26 slides along the yankauer 12, the ability to secure the sleeve 24 to the valve 26, the cost of the material, the ability of the material to provide the valve 26 with the ability to stop when engaging the yankauer 12, etc. As shown in FIGS. 1 and 2, the valve 26 may be dome-shaped so as to cover the suction tip 16 of the yankauer 12.

Figure 4:
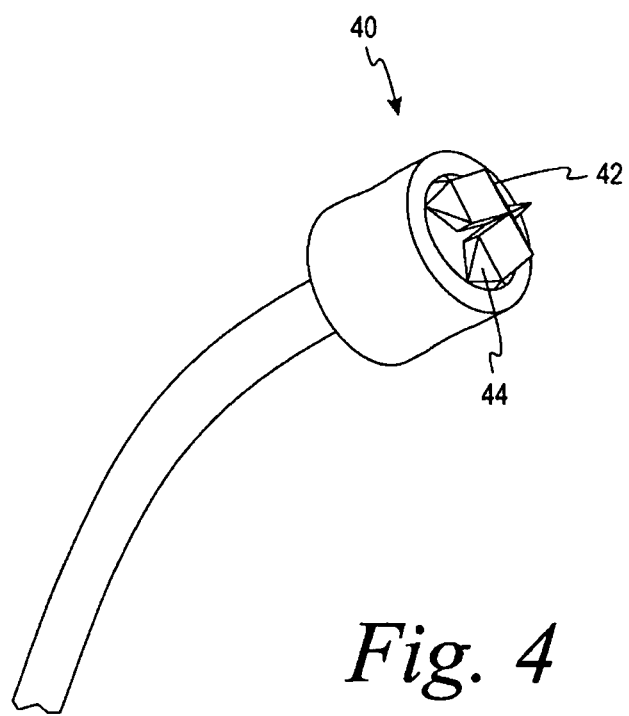
FIG. 4 is a perspective view of another embodiment of the valve.

The shape of the valve 26 along with the cross-cut 28 can vary. For example, an alternative embodiment of a valve 40 can be seen in FIG. 4. The shape chosen for the valve and cross-cut may depend on the level of friction desired when engaging the yankauer 12, the effectiveness of the valve in wiping excess secretions from the yankauer 12, the ability of the valve (and/or flaps) to form a secure closure when not engaged, etc. The valve 40 includes a cross-cut 42 and extendable opening flaps 44. In the embodiment shown in FIG. 4, the extendable opening flaps 44 have two edges that terminate adjacent to the cross-cut 42. The extendable opening flaps 44 are in the shape of a three-dimensional, indented diamond. The extendable opening flaps 44 remain closed when the yankauer 12 is not in use as shown in FIG. 4. When in use, the extendable opening flaps 44 become unindented so as to enable the extendable opening flaps 44 to slidably and frictionally engage the yankauer 12. When not in use, the flaps 44 assist to enclose the yankauer 12. The valve 40 operates in much the same way as and may be comprised of a similar material as the valve 26. It should be noted, however, the shape of the valve and of the cross-cut opening should not be limited to those disclosed in the figures. Other shapes and openings can be used such as, but not limited to, a duckbill, umbrella, diaphragm, cross-slit or other suitable shapes or openings. The valve and its opening can also be flat, inverted, protruding, recessed, etc.

Turning now to the use of the suction device, the covered yankauer suction device 10 is initially provided as illustrated in FIG. 1, with the sleeve 24 fully extended and the valve 26 enclosing the suction tip 16. The connector 14 is then connected to a vacuum source (not illustrated). When the covered yankauer suction device 10 is ready for use to aspirate secretions, the user grips and retracts the valve 26 towards the connector 14. The suction tip 16 of the yankauer 12 will push against the underside of the flaps 30, thereby protruding through cross-cut 28. The valve 26 is opened in this manner. The valve 26 is then retracted to the position shown in FIG. 2 or to any other position along the yankauer 12 so that enough of the yankauer 12 is exposed for the desired suction procedure. In one embodiment, there is about 2.5-3 inches of clearance from the tip of the valve 26 when retracted. During retraction of the valve 26, the flaps 30 are in constant contact with the yankauer 12. As such, when the valve 26 is released after retraction, the valve 26 will remain in the released position due to the contact and resulting friction between the flaps 30 and the yankauer 12. In other words, the valve 26 passively locks against the yankauer 12 once slidably engaged. This passive locking feature greatly reduces and/or eliminates the possibility of the valve 26 sliding out of place during use and adversely affecting the patient undergoing a procedure.

The vacuum source can then be activated and the covered yankauer suction device 10 will be ready for use. After use, the valve 26 is returned along the yankauer 12 towards and past the suction tip 16. As the valve 26 is returned along the yankauer 12, the flaps 30 remain in constant contact with the yankauer 12. The design of the flaps 30 enables the valve 26 to wipe any remaining secretions, exudates, irrigating and/or bodily fluids off the surface of the yankauer 12. The valve 26 automatically closes once the cross-cut 28 and the flaps 30 move past the suction tip 16. In this manner, the covered yankauer suction device 10 can be used and reused, while protecting the yankauer 12 from either passing contamination to the ambient surroundings or receiving contamination from the ambient surroundings.

Use of the yankauer suction device 40 in FIG. 4 is accomplished in much the same or similar way as that described above in relation to the yankauer suction device 10 of FIGS. 1-3.

The covered yankauer suction devices described herein may be used in a variety of procedures including, but not limited to, oral uses, surgical applications whereby clinicians desire the yankauer to be covered when not in the active suctioning mode, emergency and/or trauma applications in the field with emergency medical service staff (i.e., fire department, ambulance companies, etc.) or in hospital settings, long term care applications where respiratory suctioning may be required as in the case of a ventilated patient at home, in nursing homes or extended care facilities.

According to alternative embodiment A, a covered yankauer suction device comprises a yankauer having a suction tip at a first end and a connector at a second end, a retractable sleeve partially enclosing the yankauer, the retractable sleeve having one end secured to the yankauer and an opposite free end, and a valve secured to the free end of the retractable sleeve, the valve including a cross-cut, the cross-cut enables the valve to open when the suction tip of the yankauer pushes against an underside of the cross-cut.

According to alternative embodiment B, the covered yankauer suction device of alternative embodiment A, wherein the valve is further adapted to slidably and frictionally engage the yankauer and passively lock against the yankauer once slidably engaged.

According to alternative embodiment C, the covered yankauer suction device of alternative embodiment A, wherein the suction tip of the yankauer contains at least one aperture.

According to alternative embodiment D, the covered yankauer suction device of alternative embodiment A, wherein the suction tip of the yankauer is enclosed by the valve and the sleeve when the covered yankauer suction device is not in use.

According to alternative embodiment E, the covered yankauer suction device of alternative embodiment A, wherein the yankauer is slidably and frictionally engaged by the valve when the covered yankauer suction device is in use.

According to alternative embodiment F, the covered yankauer suction device of alternative embodiment A, wherein the valve is comprised of silicone, a thermoplastic elastomer, natural rubber (latex), polyester, nylon, polyisoprene, nitrile, urethane, or combinations thereof.

According to alternative embodiment G, the covered yankauer suction device of alternative embodiment A, wherein the covered yankauer suction device is adapted to be reused.

According to alternative embodiment H, the covered yankauer suction device of alternative embodiment A, wherein the connector is adapted to associate with a vacuum source.

According to alternative embodiment I, a covered yankauer suction device comprises a yankauer having a suction tip at a first end and a connector at a second end, a retractable sleeve partially enclosing the yankauer, the retractable sleeve having one end secured to the yankauer and an opposite free end, and a valve secured to the free end of the sleeve, the valve being adapted to slidably and frictionally engage the yankauer.

According to alternative embodiment J, the covered yankauer suction device of alternative embodiment I, wherein the suction tip of the yankauer contains at least one aperture.

According to alternative embodiment K, the covered yankauer suction device of alternative embodiment I, wherein the suction tip of the yankauer is enclosed by the valve and the sleeve when the covered yankauer suction device is not in use.

According to alternative embodiment L, the covered yankauer suction device of alternative embodiment I, wherein the yankauer is slidably and frictionally engaged by the valve when the yankauer suction device is in use.

According to alternative embodiment M, the covered yankauer suction device of alternative embodiment I, wherein the valve is comprised of silicone, a thermoplastic elastomer, natural rubber (latex), polyester, nylon, polyisopreme, nitrile, urethane, or combinations thereof.

According to alternative embodiment N, the covered yankauer suction device of alternative embodiment I, wherein the covered yankauer suction device is adapted to be reused.

According to alternative embodiment O, the covered yankauer suction device of alternative embodiment I, wherein the valve includes a cross-cut, the cross-cut enables the valve to open when the suction tip of the yankauer pushes against an underside of the cross-cut.

According to alternative embodiment P, a method for using a covered yankauer suction device, the method comprising the acts of providing a yankauer having a connector at a first end and a suction tip at a second end, a retractable sleeve partially enclosing the yankauer, the retractable sleeve having one end secured to the yankauer and an opposite free end, and a valve secured to the free end of the sleeve, gripping the yankauer near the connector, and sliding the valve along the yankauer towards the connector, the valve being adapted to passively lock to the yankauer after the sliding of the valve.

According to alternative embodiment Q, the method of alternative embodiment P, wherein the method further comprises the act of sliding the valve along the yankauer towards the suction tip.

According to alternative embodiment R, the method of alternative embodiment Q, wherein the valve is further adapted to wipe secretions from the yankauer as the valve slides towards the suction tip of the yankauer.

According to alternative embodiment S, the method of alternative embodiment P, wherein the valve is comprised of silicone, a thermoplastic elastomer, natural rubber (latex), polyester, nylon, polyisopreme, nitrile, urethane, combinations thereof.

According to alternative embodiment T, the method of alternative embodiment P, wherein the covered yankauer suction device is adapted to be reused.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A covered yankauer suction device comprising:
 a yankauer having a suction tip at a first end and a connector at a second end;
 a retractable sleeve partially enclosing the yankauer, the retractable sleeve having one end secured to the yankauer and an opposite free end; and
 a gearless valve secured to the free end of the retractable sleeve, the valve including a cross-cut, the cross-cut enables the valve to open and access to the suction tip of the yankauer when the suction tip of the yankauer pushes against an underside of the cross-cut, the valve adapted for contacting the surface of the yankauer along the length of the yankauer when the valve is retracted, and wherein the covered yankauer suction device is suitable for reuse.

2. The covered yankauer suction device of claim 1 wherein the valve is further adapted to slidably and frictionally engage the yankauer and passively lock against the yankauer once slidably engaged.

3. The covered yankauer suction device of claim 1, wherein the suction tip of the yankauer contains at least one aperture.

4. The covered yankauer suction device of claim 1, wherein the suction tip of the yankauer is enclosed by the valve and the sleeve when the covered yankauer suction device is not in use.

5. The covered yankauer suction device of claim 1, wherein the yankauer is slidably and frictionally engaged by the valve when the covered yankauer suction device is in use.

6. The covered yankauer suction device of claim 1, wherein the valve is comprised of silicone, a thermoplastic elastomer, natural rubber (latex), polyester, nylon, polyisoprene, nitrile, urethane, or combinations thereof.

7. The covered yankauer suction device of claim 1, wherein the valve is in constant contact with the yankauer and removes contaminants from the surface of the yankauer.

8. The covered yankauer suction device of claim 1, wherein the connector is adapted to associate with a vacuum source.

9. A method for using a reusable covered yankauer suction device, the method comprising the acts of:

providing a yankauer having a connector at a first end and a suction tip at a second end, a retractable sleeve partially enclosing the yankauer, the retractable sleeve having one end secured to the yankauer and an opposite free end, and a gearless valve secured to the free end of the sleeve;

gripping the yankauer near the connector; and sliding the valve along the yankauer towards the connector, the valve including a cross-cut that enables the valve to open and provides access to the suction tip of the yankauer when the suction tip of the yankauer pushes against an underside of the cross-cut, the valve being adapted to passively lock against the length of the yankauer after the sliding of the valve.

10. The method of claim 9, wherein the method further comprises the act of sliding the valve along the yankauer towards the suction tip.

11. The method of claim 10, wherein the valve is further adapted to wipe secretions from the yankauer as the valve slides towards the suction tip of the yankauer.

12. The method of claim 9, wherein the valve is comprised of silicone, a thermoplastic elastomer, natural rubber (latex), polyester, nylon, polyisopreme, nitrile, urethane, or combinations thereof.

13. The method of claim 9, wherein the covered yankauer suction device is adapted to be reused.

\* \* \* \* \*